US006584339B2

United States Patent
Galloway, Jr. et al.

(10) Patent No.: US 6,584,339 B2
(45) Date of Patent: Jun. 24, 2003

(54) METHOD AND APPARATUS FOR COLLECTING AND PROCESSING PHYSICAL SPACE DATA FOR USE WHILE PERFORMING IMAGE-GUIDED SURGERY

(75) Inventors: Robert L. Galloway, Jr., Nashville, TN (US); William C. Chapman, Nashville, TN (US); James D. Stefansic, Nashville, TN (US); Alan J. Herline, Nashville, TN (US); Candice D. Pinson, Mountain View, CA (US)

(73) Assignee: Vanderbilt University, Nashville, TN (US)

( * ) Notice: Subject to any disclaimer, the term of this patent is extended or adjusted under 35 U.S.C. 154(b) by 19 days.

(21) Appl. No.: 09/894,732

(22) Filed: Jun. 27, 2001

(65) Prior Publication Data

US 2003/0000535 A1 Jan. 2, 2003

(51) Int. Cl.[7] ............................................... A61B 5/055
(52) U.S. Cl. ........................................ 600/426; 600/429
(58) Field of Search ............................... 600/426, 410, 600/411, 424, 425, 429, 443, 439, 437

(56) References Cited

U.S. PATENT DOCUMENTS

| 5,383,454 A | 1/1995 | Bucholz |
| 5,647,361 A | 7/1997 | Damadian |
| D387,427 S | 12/1997 | Bucholz et al. |
| 5,817,105 A | 10/1998 | Van Der Brug |
| 5,851,183 A | 12/1998 | Bucholz |
| 5,871,445 A | 2/1999 | Bucholz |
| 5,891,034 A | 4/1999 | Bucholz |
| 5,970,499 A | 10/1999 | Smith et al. |
| 5,980,535 A | 11/1999 | Barnett et al. |
| 5,987,960 A | 11/1999 | Messner et al. |
| 6,013,087 A | 1/2000 | Adams et al. |
| D420,132 S | 2/2000 | Bucholz et al. |
| 6,021,343 A | 2/2000 | Foley et al. |
| 6,038,467 A | 3/2000 | De Bliek et al. |
| D422,706 S | 4/2000 | Bucholz et al. |
| 6,045,532 A | 4/2000 | Eggers et al. |
| 6,066,123 A | 5/2000 | Li et al. |
| 6,066,134 A | 5/2000 | Eggers et al. |
| 6,076,008 A | 6/2000 | Bucholz |
| 6,112,113 A | 8/2000 | Van Der Brug et al. |
| 6,135,946 A | 10/2000 | Konen et al. |
| 6,161,033 A | 12/2000 | Kuhn |
| 6,167,292 A | 12/2000 | Badano et al. |
| 6,187,018 B1 | 2/2001 | Sanjay-Gopal et al. |
| 6,195,577 B1 | 2/2001 | Truwit et al. |

(List continued on next page.)

OTHER PUBLICATIONS

Stefansic et al., "Interactive, Image–Guided Hepatic Surgery," Part of the SPIE Conference on Image Display, pp. 241–251, (Feb., 1999).

Herline et al., "Surface Registration For Use In Interactive, Image–Guided Liver Surgery," Presented at the Second International Medical Image Computing and Computer–Assisted Intervention (MICCAI) Conference, 16 pp., (Sep., 1999).

(List continued on next page.)

Primary Examiner—Hieu T. Vo (57) ABSTRACT

A method and apparatus for collecting and processing physical space data used while performing image-guided surgery is disclosed. Physical space data is collected by probing physical surface points of surgically exposed tissue. The physical space data provides three-dimensional (3-D) coordinates for each of the physical surface points. Based on the physical space data collected, point-based registrations used to indicate surgical position in both image space and physical space are determined. The registrations are used to map into image space, image data describing the physical space of an ablative instrument used to perform the image-guided surgery, an ablation zone of the instrument, the surgically exposed tissue, and a particular portion of the tissue to be resected or ablated. The image data is updated on a periodic basis.

40 Claims, 5 Drawing Sheets

U.S. PATENT DOCUMENTS 6,236,875 B1    5/2001   Bucholz et al.
6,259,943 B1 *  7/2001   Cosman et al. ............. 600/429
6,374,135 B1 *  4/2002   Bucholz ..................... 600/427
6,490,475 B1 * 12/2002   Seeley et al. ............... 600/426

OTHER PUBLICATIONS

Stefansic et al., "Registration Of Physical Space To Laparoscopic Image Space For Use In Minimally Invasive Hepatic Surgery," IEEE Transactions on Medical Imaging, vol. 19, No. 10, pp. 1012–1023, (Oct., 2000).

Beasley et al., "Implementation And Incorporation Of Liver 3–D Surface Renderings Into Interactive, Image–Guided Hepatic Surgery," Proc. of SPIE vol. 3976, Image Display and Visualization, pp. 282–289, (Feb. 2000).

Galloway et al., "Task–Oriented Asymmetric Multiprocessing For Interactive Image–Guided Surgery," Parallel Computing 24, pp. 1323–1343, (1998).

Oncology News International, "Radiofrequency Ablation Used To Treat Liver Metastases," vol. 8, No. 10, (Oct., 1999).

Patterson, Sunita, "Promising Radio Frequency Treatment—New Option For Patients With Unresectable Liver Tumors," OncoLog, vol. 43, No. 3 (Mar., 1998).

* cited by examiner

METHOD AND APPARATUS FOR COLLECTING AND PROCESSING PHYSICAL SPACE DATA FOR USE WHILE PERFORMING IMAGE-GUIDED SURGERY

STATEMENT REGARDING FEDERALLY SPONSORED RESEARCH OR DEVELOPMENT

This work was supported in part by grants from the National Institutes of Health (NIH) and the National Science Foundation (NSF) (NIH grants NIGMS GM52798 and NRSA #1 F32 DK 09671-01 SB; and NSF grant BES-9703714) and the U.S. Government may therefore have certain rights in this invention.

BACKGROUND OF THE INVENTION

1. Field of the Invention

The present invention relates to using image-guided surgery techniques to collect data to insure accurate tracking of an ablation device.

2. Background Information

For over fifty years, diagnostic images have been used for surgical guidance, especially in the field of neurosurgery. Image-guided surgery implements two fundamental ideas: first, the concept of an image-space to physical-space mapping or registration, and second, the use of an extracranial device for accurate surgical guidance without direct visualization. Such ideas gave birth to stereotactic neurosurgery, a technique for locating targets of surgical interest within the brain relative to an external frame of reference. This is traditionally defined as the temporary attachment of a mechanical frame to the skull or scalp in order to define a 3-D frame space around a patient. With the advent of computed tomography (CT), the coordinates of a target (i.e. tumor) in image space could be assigned coordinates in frame space if the CT images were obtained with the attached frame. Unfortunately, frames are uncomfortable to patients, must be applied prior to imaging, and are cumbersome in the imaging environment and the operating room.

These factors led to the development of frameless stereotactic surgical systems, or interactive, image-guided surgery (IIGS) systems. In traditional IIGS systems, present surgical position is tracked during an operation and displayed on pre-operatively obtained tomographic images. As the surgeon changes the current surgical position, displayed images are updated in real time. In one of the earliest IIGS systems, physical space surgical position was determined using articulated arms. The position of an articulated pointer was calculated using a personal computer (PC) and overlayed on tomographic images. Magnetic resonance images (MRI) and CT negative films were scanned into the computer and displayed as images on a video interface. Other early image-guided surgical systems also used electromechanical 3-D coordinate digitizers to indicate present surgical position on various representations of patient data, including 2-D transverse, coronal and sagittal CT or MRI slices, and on image renderings of the physical object surface. Since it was necessary to have computers capable of managing large volumes of image information (>100 Mbytes) and updating the display quickly, most early IIGS systems were developed with VME bus devices running UNIX.

Early IIGS systems were developed on PCs using multiple processors. In a task-oriented asymmetric multiprocessing (TOAM) system developed in 32 bit extended DOS, discrete tasks such as physical space localization, data fetching, and display were conducted asynchronously on specialized processors which communicated with inexpensive, general purpose processors that worked as loaders and schedulers. For physical space localization, several articulated arms with six degrees of freedom were first developed. These cumbersome arm devices were eventually replaced with lightweight cylindrical pen-like probes which could be tracked more easily in the operating room using an optical triangulation system. The spatial location of the guidance instrument was determined using a collection of discrete processors which continually update the physical space location. This location was then passed to the central processor where it was mapped into image space. Once the image space map was complete, the appropriate tomographic slices were selected and displayed. Because this system was designed before the advent of large memory availability, image display relied heavily on hardware manipulation using disk controllers to load images directly from the hard drive. Control of the bus was passed from the main processor to the disk drive controller, where the correct image was fetched and sent to the display processor.

With the continuing increase in performance to price, processes which could only be performed on workstation class machines are now routinely performed on PCs. As the PC hardware evolved, however, it became apparent that DOS-based systems would not have the continuing support of hardware vendors.

Because of these considerations, a need for an operating room image-oriented navigation system (ORION) emerged. ORION was developed in Windows NT using MS Visual C++ 6.0 with the Win32 API. Not only was this system designed to be faster than the previous one, but it was not necessary to redesign the software with each hardware advance. Components of the system were developed as dynamic link libraries (DLLs), so that new technology could be incorporated into the system without a complete software rewrite. The system is also somewhat portable. It runs adequately on any PC with a 200 MHz or higher Pentium processor and 128 MB of memory which also has the appropriate video card and 3-D localizer hardware and software.

When designing an image-guided surgical system, it is critical that the precise location of an ablative instrument used to perform image-guided surgery be determined on a continuous basis (e.g., update rates approaching 30 frames per second). Further, in an effort to insure the utmost in precision, an ablation zone of the ablative instrument, the tissue being operated on, and a particular portion of the tissue to be resected or ablated during surgery must also be continuously and accurately tracked.

What is needed is a method and apparatus for collecting and processing physical space data for use while performing image-guided surgery, such that tumors and lesions in the tissue of a living patient can be accurately located, and resected or ablated with a precisely tracked ablative instrument. The present invention fulfills such a need.

BRIEF SUMMARY OF THE INVENTION

In interactive, image-guided surgery, current physical space position in the operating room is displayed on various sets of medical images used for surgical navigation. The present invention is a PC-based surgical guidance system which synchronously displays surgical position on up to four image sets and updates them in real time. There are three essential components and techniques which have been developed for this system: 1) accurately tracked ablative instruments, 2) accurate registration techniques to map physical space to image space, and 3) methods and apparatus to display and update the image sets on a computer monitor. For each of these components, a set of dynamic link libraries has been developed in MS Visual C++ 6.0 supporting various hardware tools and software techniques. Surgical (i.e., ablative) instruments are tracked in physical space using an active optical tracking system. Several different registration algorithms were developed with a library of robust math kernel functions, and the accuracy of all registration techniques have been thoroughly investigated. The present invention was developed using the Win32 API for windows management and tomographic visualization, a frame grabber for live video capture, and OpenGL for visualization of surface renderings. This current implementation of the present invention can be used for several surgical procedures, including open and minimally invasive liver surgery.

In a method according to the present invention, physical space data is collected and processed for use while performing image-guided surgery. Tissue of a living patient is surgically exposed. Physical space data is then collected by probing a plurality of physical surface points of the exposed tissue, the physical space data providing three-dimensional (3-D) coordinates for each of the physical surface points. Based on the physical space data collected, point-based registrations used to indicate surgical position in both image space and physical space are determined. The registrations are used to map into image space, image data describing the physical space of an ablative instrument used to perform the image-guided surgery, an ablation zone of the instrument, the tissue, and a particular portion of the tissue to be resected or ablated. The image data is updated on a periodic basis.

The collection of physical space data may be performed by sweeping an optically tracked localization probe over the surface of the exposed tissue. The tissue may be the patient's liver and the particular portion of tissue to be resected or ablated may be a hepatic metastatic tumor.

Prior to surgery, tissue of the patient may be scanned to acquire, store and process a 3-D description of the organ or structure of interest (e.g., a 3-D reference). A triangularized mesh may be created based on the scanned tissue. The volumetric center of a particular portion of the tissue to be resected or ablated during the surgery may be determined, wherein an algorithm using the triangularized mesh and the collected physical space data may be implemented to determine the point-based registrations. The algorithm may be a Besl and Mackay iterative closest point (ICP) registration algorithm.

The scanning of the tissue may be performed by one of a computerized tomography (CT) scanner, a magnetic resonance imaging (MRI) scanner and a positron emission tomography (PET) scanner.

The ablative instrument may emit a plurality of intermittent infrared signals used to triangulate the position of the ablative instrument in 3-D image space. The signals may be emitted from a plurality of infrared emitting diodes (IREDs) distributed over the surface of a handle of the ablative instrument in a spiraling fashion. The IREDs may flash in time sequence. Each IRED may have a 60 degree transmission angle.

The image data may be updated in real time at 30 Hz or greater. The ablative instrument may use one of radio-frequency and cryoablation to resect or ablate the particular portion of the tissue. The ablative instrument may have a tip comprising an ablation device. The ablation zone may extend 1 centimeter from the tip of the ablative instrument.

Information from the localizer may also be used in conjunction with laparoscopic or endoscopic imaging. Points from 3-D physical space may be mapped to 2-dimensional (2-D) image space. Points from 3-D physical space may be mapped to 2-dimensional (2-D) laparoscopic video space using a direct linear transformation (DLT). Points from 3-D physical space may be mapped to 3-D tomographic image space. Points from 3-D physical space may be mapped to 2-dimensional (2-D) endoscopic image space.

In an apparatus according to the present invention, physical space data is collected and processed for use while performing image-guided surgery. The apparatus comprises a probe instrument, an ablative instrument and an image data processor. The probe instrument collects physical space data by probing a plurality of physical surface points of surgically exposed tissue of a living patient. The physical space data provides three-dimensional (3-D) coordinates for each of the physical surface points. The ablative instrument may resect or ablate a particular portion of the exposed tissue.

The image data processor comprises a computer-readable medium holding computer-executable instructions which, based on the physical space data collected by the probe instrument, determine point-based registrations used to indicate surgical position in both image space and physical space. Using the point-based registrations to map into image space, image data describing the physical space of an ablative instrument used to perform the image-guided surgery, an ablation zone of the ablative instrument, the tissue, and a particular portion of the tissue to be resected or ablated. The image data is updated on a periodic basis.

The probe instrument may be swept over the surface of the exposed tissue. The apparatus may also comprise a scanning device for scanning tissue of the patient to acquire, store and process a 3-D reference of tissue prior to the tissue being surgically exposed. The image data processor creates a triangularized mesh based on the scanned tissue, determines the volumetric center of a particular portion of the tissue to be resected or ablated during the surgery, and implements an algorithm using the triangularized mesh and the physical space data collected by the probe instrument to determine the point-based registrations. The algorithm is a Besl and Mackay iterative closest point (ICP) registration algorithm.

The scanning device may be one of the following scanners: a computerized tomography (CT) scanner, a magnetic resonance imaging (MRI) scanner and a positron emission tomography (PET) scanner.

The ablative instrument may emit a plurality of intermittent infrared signals used to triangulate the position of the ablative instrument in 3-D image space, the signals being emitted from a plurality of infrared emitting diodes (IREDs) distributed over the surface of a handle of the ablative instrument in a spiraling fashion. The IREDs may flash in time sequence. Each IRED may have a 60 degree transmission angle. The image data may be updated in real time at 30 Hz or greater.

The ablative instrument may use one of radio-frequency and cryoablation to resect or ablate the particular portion of the tissue. The ablative instrument may have a tip comprising an ablation device. The ablation zone may extend 1 centimeter from the tip of the ablative instrument.

Points from 3-D physical space may be mapped to 2-dimensional (2-D) image space. Points from 3-D physical space may be mapped to 2-dimensional (2-D) laparoscopic video space using a direct linear transformation (DLT).

Points from 3-D physical space may be mapped to 3-D tomographic image space. Points from 3-D physical space may be mapped to 2-dimensional (2-D) endoscopic image space.

BRIEF DESCRIPTION OF THE SEVERAL VIEWS OF THE DRAWINGS

The following detailed description of preferred embodiments of the present invention would be better understood when read in conjunction with the appended drawings. For the purpose of illustrating the present invention, there are shown in the drawings embodiments which are presently preferred. However, the present invention is not limited to the precise arrangements and instrumentalities shown. In the drawings.

DETAILED DESCRIPTION OF THE INVENTION

Figure 1:
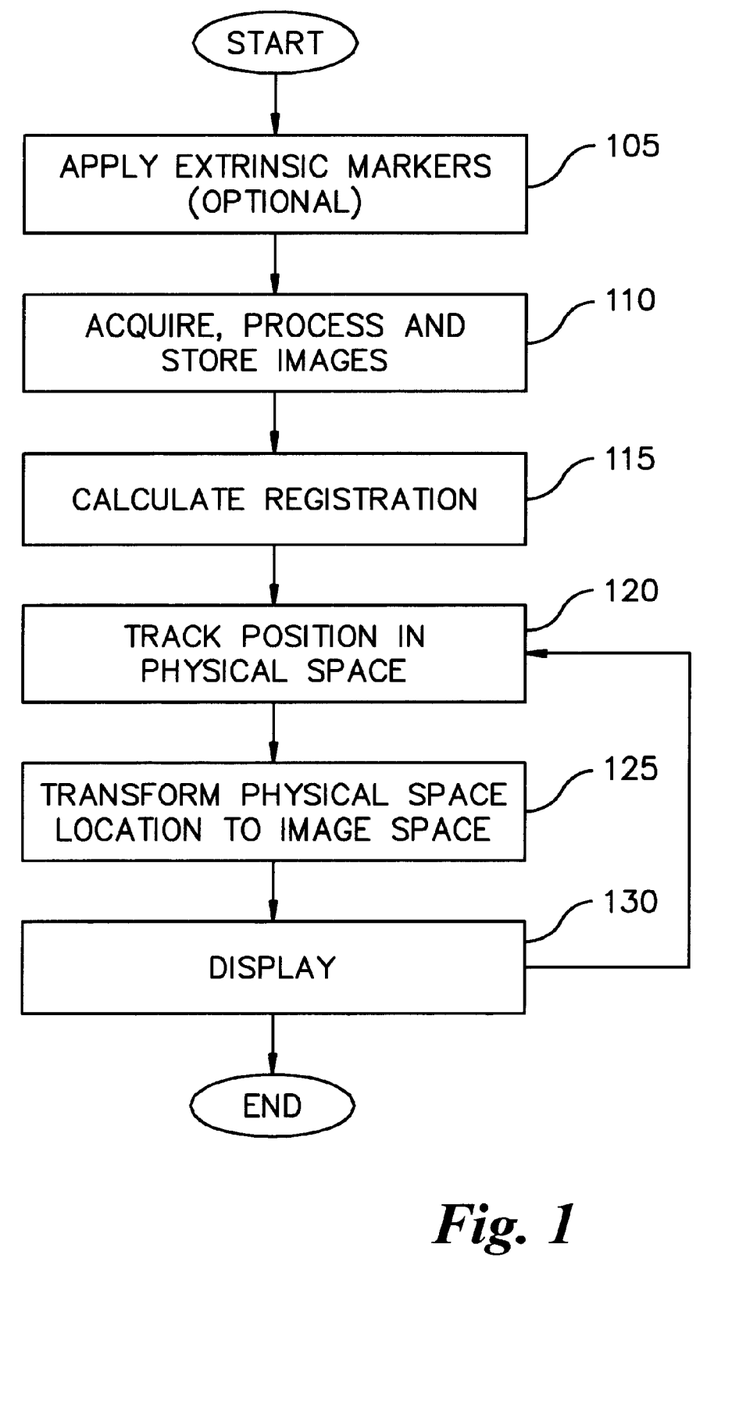
FIG. 1 shows a general flow chart in accordance with the present invention.

FIG. 1 shows some of the major events involved in preparing for and performing IIGS. In step 105, it is determined if any extrinsic markers will be attached to the patient. These makers, or fiducials, are designed to be imaged and then localized in both image space and physical space for use in a point-based registration algorithm. Appropriate image volumes for a patient are then acquired, stored and processed (step 110). Most image volumes are acquired as a set of slices, 256×256 or 512×512 pixels per slice at 2 bytes per pixel with 20–200 images per volume. These images are acquired on a computerized tomography (CT) scanner, a magnetic resonance imaging (MRI) scanner or a positron emission tomography (PET) scanner. Images are typically transferred from PACS servers in radiology to image-guided surgical computers, where they are processed for display before surgery if necessary. Transverse, sagittal, or coronal tomographic slices require minor processing before display. In order to visualize surface renderings, a triangulated surface can be created from the volume and displayed. These triangulated surfaces can also be used in registration algorithms to map a physical surface to an image surface.

Once the surgeon has prepared and positioned the patient for surgery, it is necessary to register or map patient or physical space to image space before images can be used interactively (step 115). Physical space data is collected using an instrument whose position is tracked in the operating room. For point-based registrations, corresponding points that can be localized accurately in both image space and physical space are used to create the mapping. These can include extrinsic fiducials that were attached to the patient before imaging or intrinsic fiducials which include anatomic landmarks visible in both physical and image space. For surface-based registrations, a surface of physical space points is collected and mapped onto a triangulated surface. After the accuracy of the registration is assessed, the tracked instrument is moved in physical space and the corresponding position in image space is displayed (steps 120, 125 and 130) and used as a guide during the surgical procedure.

In order to carry out the tasks of determining the location of a tracked probe in space, registering that position into image space, and displaying the appropriate image or images on a computer screen, three divisions of run-time dynamic link libraries (DLLs) were initially developed for our system. The first is a localizer division, which is responsible for determining current surgical position based on the location of an instrument in space. The second is a registration division, which calculates accurate mappings between image space and physical space. The third is a display division, which displays various types of medical images on the computer screen. By separating the system into several DLL divisions, the present invention allows for modularity. Depending on a particular surgical case, for instance, a surgeon may choose one type of localizer, one or more types of displays, and one or more types of registration to indicate surgical position on the images.

Because an image-guided surgical system is, by definition, used in surgery by surgeons and surgical staff, the present invention has an intuitive interface and display to minimize the potential for distraction. Using a simple push-button interface, a patient is selected from the database, physical space data is collected, and a registration between physical space and image space is calculated. Images are then selected and displayed in one of four quadrants on the screen and updated as surgical position changes.

A surgeon can use the present invention for guidance in extremely delicate procedures, such as removing a tumor from a sensitive region of the brain or resect multiple lesions in regions of the liver near major blood vessels. It is important that current surgical position displayed on medical images be as close to actual surgical position as possible. It is also imperative that the images are updated quickly, since a surgeon may change his or her current location rapidly in order to gather spatial information about a certain structure and its surroundings. Accordingly, there are two performance goals in the development of the present invention: accuracy and speed. It is necessary to develop accurate, automatic registration algorithms to map physical space to image space. These algorithms should also be computationally efficient since time constraints are always a concern in surgical applications. It is also important to develop accurately tracked instruments to indicate current surgical position in physical space. Once the registration is calculated and instrument location is mapped into image space, it is necessary to update the images as fast as possible, since surgeons are sensitive to display speed. One of the worst possible scenarios would be for the surgeon to move the probe and make a decision based on the current display, only to find that the display indicated a previous position. A true image-guided surgical system should update images in real time at 30 Hz as surgical position changes.

Figure 2:
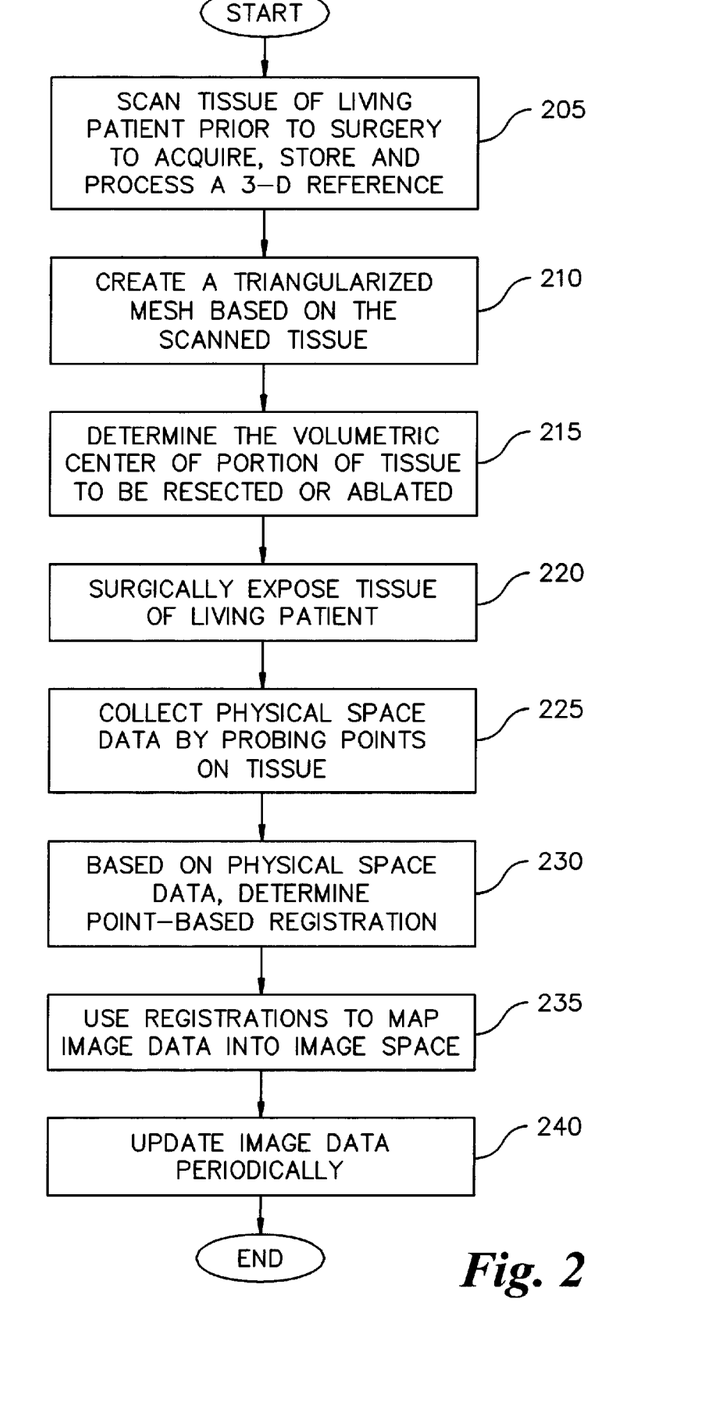
FIG. 2 shows a detailed flow chart illustrating how collected and processed physical space data is used to perform image-guided surgery in accordance with the present invention.

The present invention collects and processes physical space data for use while performing image-guided surgery, as illustrated in the flow chart of FIG. 2. Prior to surgery, tissue of the patient is scanned to acquire, store and process a 3-D reference (step 205). A triangularized mesh is then created based on the scanned tissue (step 210). The volumetric center of a particular portion of the tissue to be resected or ablated during the surgery is determined, wherein an algorithm using the triangularized mesh and the collected physical space data may be implemented to determine the point-based registrations (step 215). The algorithm may be a Besl and Mackay iterative closest point (ICP) registration algorithm.

Tissue of a living patient is then surgically exposed (step 220). Physical space data is then collected by probing a plurality of physical surface points of the exposed tissue, the physical space data providing three-dimensional (3-D) coordinates for each of the physical surface points (step 225). Based on the physical space data collected, point-based registrations used to indicate surgical position in both image space and physical space are determined (step 230). The registrations are used to map into image space, image data describing the physical space of an ablative instrument used to perform the image-guided surgery, an ablation zone of the instrument, the tissue, and a particular portion of the tissue to be resected or ablated (step 235). The image data is updated on a periodic basis (step 240).

Figure 3:
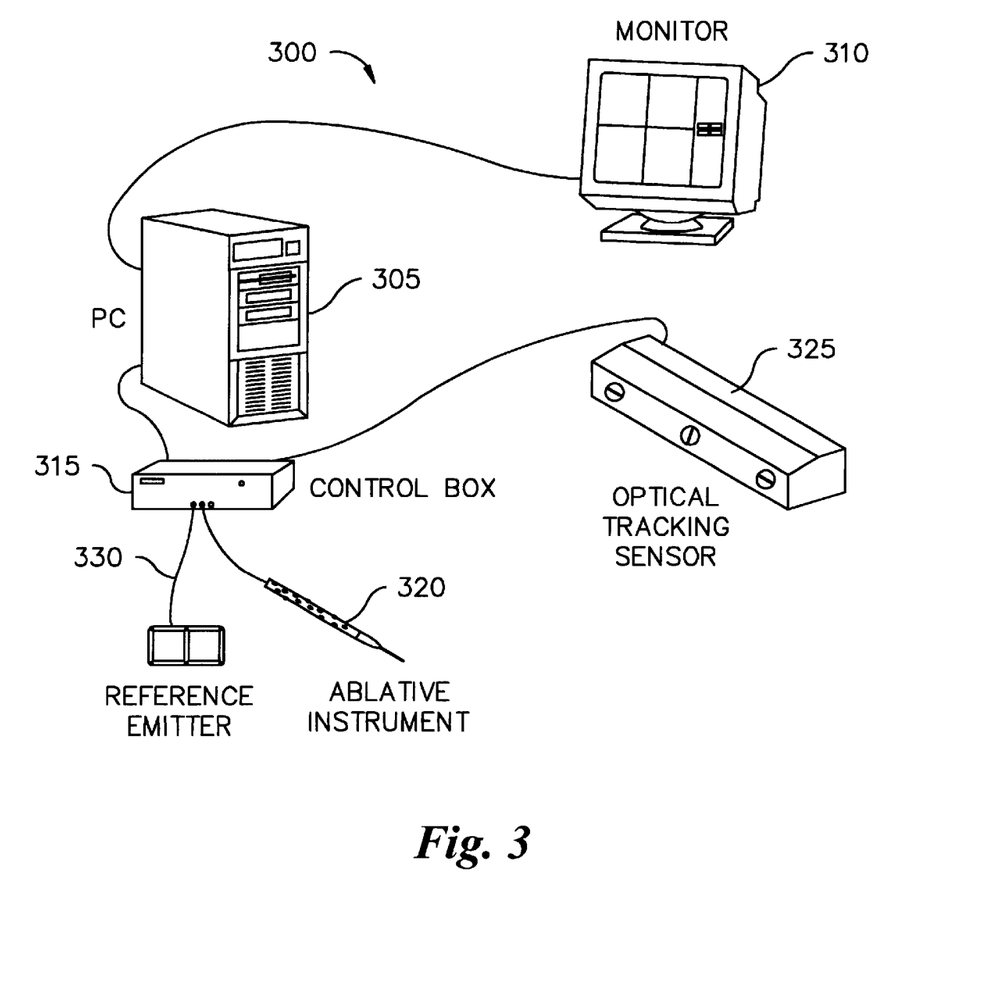
FIG. 3 shows the hardware system configuration of the present invention.

FIG. 3 shows the hardware system configuration 300 of the present invention. ORION was developed in Windows NT and is currently running on a 400 MHz processor Micron PC (an image data processor) 305 with 256 MB of memory and a display monitor 310. The display mode is 1280×1024 mode. This computer also contains two specialized cards. The VigraVision-PCI card (VisiCom Inc., Burlington, Vt.) is a combination color frame grabber and accelerated SVGA display controller which is capable of displaying NTSC video images in real time. An ISA high-speed serial port card communicates with the optical localization probe 320 via control box 315. Additional hardware for implementing the present invention include an optical tracking sensor 325, optical localization probe(s) 320, and an optical reference emitter 330.

Other paradigms for indicating surgical position could be used, including articulated arms. One preferred localization tool for use with the present invention is the Optotrak 3020 (Northern Digital Inc., Waterloo, Ontario). The optical tracking sensor 325 contains three cylindrical lenses which receive light from sequentially strobed infrared light-emitting diodes (IREDs). Triangulation is used to find each IRED relative to the position of the optical tracking sensor 325.

In order for the position and orientation of ablative instrument 320 to be measured by the optical tracking sensor 325, the ablative instrument must have a handle (rigid body) with multiple IREDs distributed over the surface of a handle of the ablative instrument 320 so that at least three IREDs are visible in all of the appropriate orientations of the ablative instrument 320. If three or more IREDs attached to the handle of the ablative instrument 320 are detected by the lenses of the optical tracking sensor 325, the tip and ablation zone of the ablative instrument 320 can be accurately localized in physical space without placing constraints on how the ablative instrument 320 needs to be handled by the surgeon.

The typical ablative instrument 320 used in neurosurgical applications has 24 IREDs which spiral around the instrument's handle. It is appropriate for use as a surgical pointer because it is light, easily directed and is extremely accurate with a tip location error of 0.35 mm in 3-D space. For endoscopic applications, a special rigid body was created for ablative instrument 320 which is more sensitive to roll for more complex manipulations. This 24 IRED "ovoid structure" attached to the endoscope weighs less than 200 g (adding less than 10% to the weight of a typical endoscope). The tip of the endoscope may be tracked with an accuracy of approximately 1.2 mm. An optically tracked radiofrequency probe is placed within the center of tumors, where it is used to microwave or heat-kill lesions. The present invention is able to track the tip of this device with an accuracy of 3.0 mm.

For surgical applications using the present invention, an ablative instrument 320 is used which not only defines a coordinate system in physical space but also preserves the registration if the patient is moved. The optical tracking sensor 325 can localize both the ablative instrument 320 and the reference emitter 330 in sensor unit space. By mapping the position of the ablative instrument 320 into the space defined by the position and orientation of the reference emitter 330, the location of the optical tracking sensor 325 drops out of the equations. The optical tracking sensor 325 can be flexibly placed before surgery and moved during the procedure to accommodate any surgical requirements.

All of the image-guided surgical software in accordance with the present invention was written using Visual C++ 6.0 in Windows NT 4.0. Because the Win32 API offers the greatest versatility in exploiting the features of Windows, this interface was chosen to create and manage the windows created in the system.

The present invention incorporates an executable program of a software system which contains the main entry point to the Windows program. Windows NT passes all user input to programs in the form of messages. Thus, the present invention implements a message pump that receives and dispatches these messages to the appropriate message handler(s). At startup, the present invention is responsible for initializing the image-guided surgery system. This task involves creating and managing the four 512×512 child windows used for image display, saving log information with the time and date the system is run, and loading the dynamic link libraries (DLLs). After initialization, the message pump in the present invention is responsible for receiving and dispatching any messages in the queue. If no messages are present, it sends information concerning the current position of the localized instrument(s) to the child windows.

Figure 4:
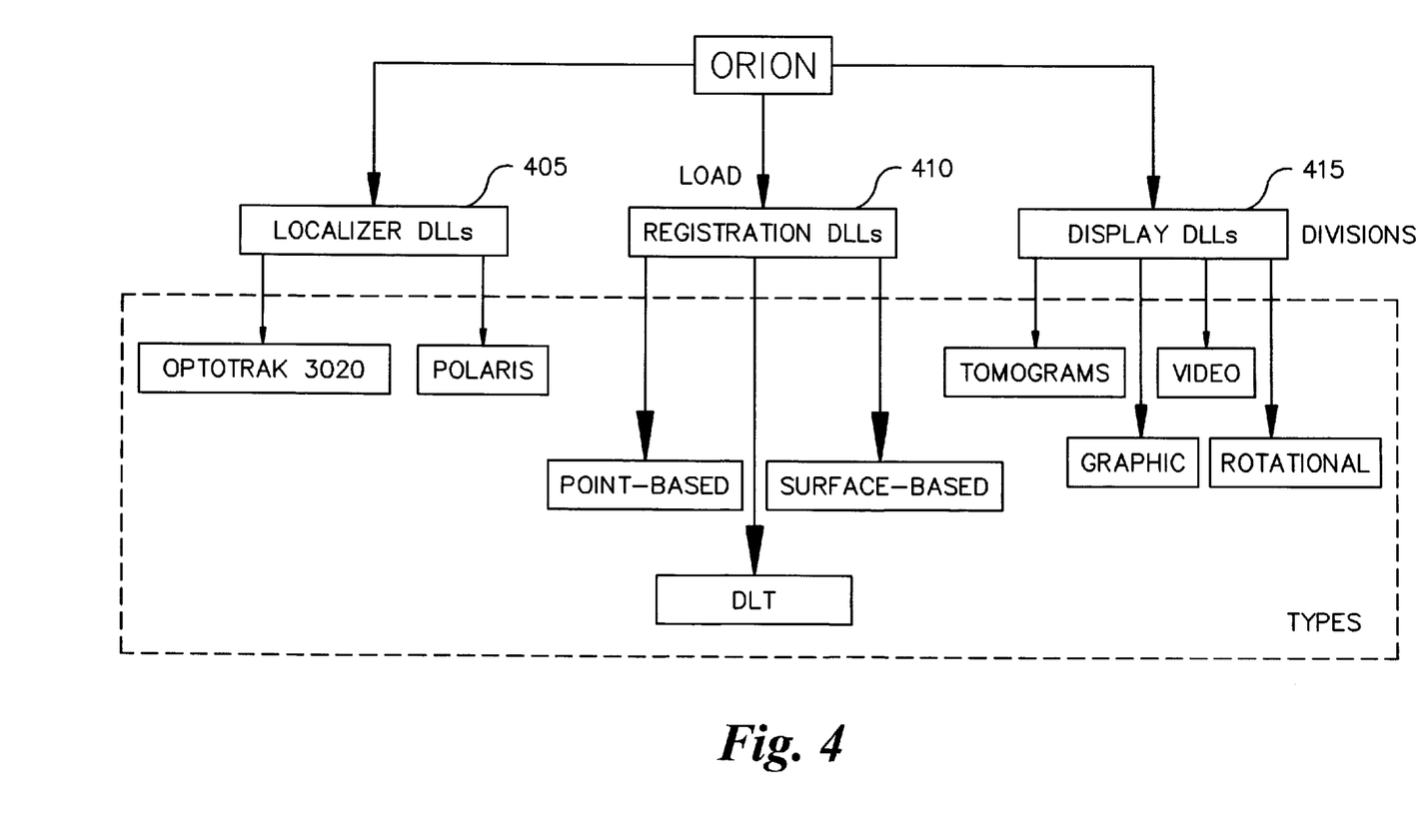
FIG. 4 shows the basic software architecture of the present invention, including the three divisions of run-time dynamic link libraries.

FIG. 4 shows the basic software architecture of the present invention, including the three divisions of run-time dynamic link libraries. For each of the three divisions, a core set of functions and structures define an interface to the DLLs. The interface represents the functionality that is required to interoperate with the present invention. Any additional functionality present within the DLL is expected to be specific to that individual DLL and not visible to the present invention. There are two functions that are common to all of the DLL interfaces, one which can be called by the present invention to receive a message related to the most recent error that occurred within the library, and another which is called to receive the identification tag for a particular type of DLL. A brief description of DLL division structure is included in the sections below, along with details about the development of particular types within a division.

The localizer division 405 consists of all the DLLs developed to track the position of instruments in physical space. The DLL interface for this division defines a common communication mechanism to various hardware devices which typically rely on vendor-supplied custom APIs for device communication. The task of implementing a localizer DLL is therefore largely a matter of grouping the API functions of the vendor into the required localizer interface functions, and ensuring correct data type conversion and error handling. A single localizer DLL is selected at startup, and all communications are performed through the interface.

Currently, localizer DLL 405 is written for the Optotrak 3020 system described previously using the Northern Digital software libraries. Several instruments can be tracked in space at once, if necessary. A function in the DLL returns 4×4 matrices that indicate the position and orientation of the optically tracked instrument(s). If either the tracked instrument(s) or the reference rigid body are blocked from the camera view or are unable to be localized with a certain accuracy, an error message is generated and the user is notified. Individual points can be collected with the Optotrak and stored in a file for use in registration algorithms or other analysis, and an entire set of data points can be collected as well. DLLs may be used for other optical tracking devices, such as the Polaris system from Northern Digital, or other non-optical systems, such as articulated arms.

The registration division 410 consists of all DLLs developed to perform registrations between image space and physical space. A generalized user interface (not shown) is used to select physical and image data models to be passed to the appropriate registration DLL. Within the individual DLLs, specific registration algorithms are used to calculate a mapping between the data sets. The interface of the present invention also allows multiple registrations for a given data set, if desired.

Two point-based registration DLLs map 3-D physical space into 3-D image space using rigid body transformations. One DLL finds a closed-form solution based on unit quaternions to create this transformation matrix. The other DLL uses singular value decomposition (SVD) to find the closed-form solution. In order to determine the transformation matrix, both algorithms require the localization of three or more corresponding non-colinear fiducial points in both 3-D spaces. The SVD algorithm is implemented using the Intel Math Kernel Library, which contains a set of robust math kernel functions that are performance optimized for Pentium processors. Another DLL implements a projective registration algorithm based on the direct linear transformation (DLT). If 6 or more non-coplanar fiducials are accurately localized in the two spaces, a projective registration between 3-D physical space and 2-D endoscopic video space can be created. The Intel library is used to calculate the SVD utilized in the DLT registration. A surface-based registration DLL based on the iterative closest-point algorithm of Besl and McKay is performed using the present invention.

One performance goal of the present invention is to develop accurate registration algorithms. For the rigid body point-based registrations, two measures of error are defined. The residual error determined in mapping the fiducial points from one 3-D space to the other is called fiducial registration error (FRE). If a mapped point not used in the creation of the transformation matrix is compared to its actual position, the difference is referred to as target registration error (TRE). For 600 neurosurgical applications conducted using externally attached fiducial markers for registration purposes, the mean TRE in mapping from physical space to CT image space was 0.67±0.25 mm, with a worse case of 1.15 mm. The accuracy of the DLT registration algorithm used to project 3-D physical space into endoscopic video space has been investigated, and it has been found that registration accuracy improves as more fiducials are used to calculate the transformation matrix. When 11 fiducials are utilized in the computation of the DLT, average TRE is 0.70 mm. Considerable work has been performed in quantifying the accuracy of many other types of registrations as well. All of the registration DLLs developed will return an appropriate quality of fit measure which helps indicate the accuracy of the registration technique(s) utilized in the surgical procedure. If the registration is point-based, a TRE/FRE metric is used for assessing registration quality. If the registration is surface-based, a new metric has been developed which includes holding out certain subsurfaces from inclusion in the registration process. These surfaces are then used as an independent check of registration quality, along with visual assessment.

The display division 415 consists of all the DLLs necessary to display any type of medical image. Two display DLLs have been developed, one type for the display of any tomographic image (MR, CT, PET), and another type for the display of any NTSC video image.

For each child window displaying a tomographic view, a device independent bitmap (DIB) is created. Images are displayed through a bit-block transfer of 8 bit data corresponding to a rectangle of pixels from the specified source device context into a destination device context (i.e., one of the four child windows).

Since most medical images are represented using 4096 individual gray levels (12 bits) and standard video hardware can only display 256 different gray levels (8 bits), some form of compression must be implemented. The compression used by the present invention is piecewise linear and is defined by the window and level parameters. The level parameter determines the uncompressed intensity that is mapped to the middle gray level. The window parameter describes the range of uncompressed intensities surrounding the level value that are mapped to shades of gray. Anything below this window is mapped to black (zero intensity) and anything above the window is mapped as white (full intensity). Tomographic images utilized during surgery are loaded into memory and saved in one of two formats depending on the desired method of display. In one format, the 12 bit/pixel grayscale images are temporarily loaded into memory and compressed to 8 bits/pixel based on the default window and level. The 12 bit images are deleted and the 8 bit images are stored in memory. When the position of the tracked instrument is moved, the appropriate 8 bit image is displayed using a bit-block transfer. Images displayed using this method are updated at greater than 30 Hz when all four windows are displaying tomograms. If the window and level of an image is changed, the entire corresponding volume must be reloaded and each image in the volume is compressed to 8 bits using the new values. The time required to compress the images with the updated window and level varies with the size and quantity of the images. Since a surgeon may want to change the window and level of an image set multiple times during a procedure in order to view different structures more clearly, a second alternative display method may be implemented.

In the alternative display method, the 12 bit volume is loaded just once. Once an appropriate image is selected for viewing, its 12 bit data is compressed to 8 bits based on the given window and level and the resulting DIEB is displayed. This "compress on the fly" method allows images to be windowed and leveled without reloading the entire corresponding volume. On our 400 MHz PC, images displayed using this method are updated at 15–20 Hz when all four windows are displaying tomograms. Either method can currently be used for display during surgery. As faster processors are developed, the "compress on the fly" method will update tomograms at an acceptable speed (>30 Hz) to meet performance goals of the present invention and the first method will be eliminated.

Cropped NTSC video images (512×480) are captured with the VigraVision-PCI color frame grabber. This can be used to display an endoscopic or intraoperative ultrasound (IOUS) view. One video image can be updated at 30 Hz in any of the four quadrants. A still video image can be captured and stored in one of several formats, such as a TIFF or a bitmap. When the image is frozen, the position and orientation of the tracked endoscope or IOUS can be saved, and points on the image can be localized and used for projective registration purposes.

Several new display DLLs have been developed for surgical applications. In a graphics DLL, an OpenGL, a 3-D graphics library, is used to render object surfaces created from triangulated tomographic volumes. Tumors or other structures segmented from these volumes can be also rendered and projected onto the object surface to aid in localization. For surgical applications, the rendering view is updated "on the fly" as surgical position is changed. In the rotation DLL, renderings and vascular projection images are created pre-operatively and the desired angular projection is displayed. The position of the probe and trajectory information is projected onto the view according to the reconstruction angle.

Figure 5:
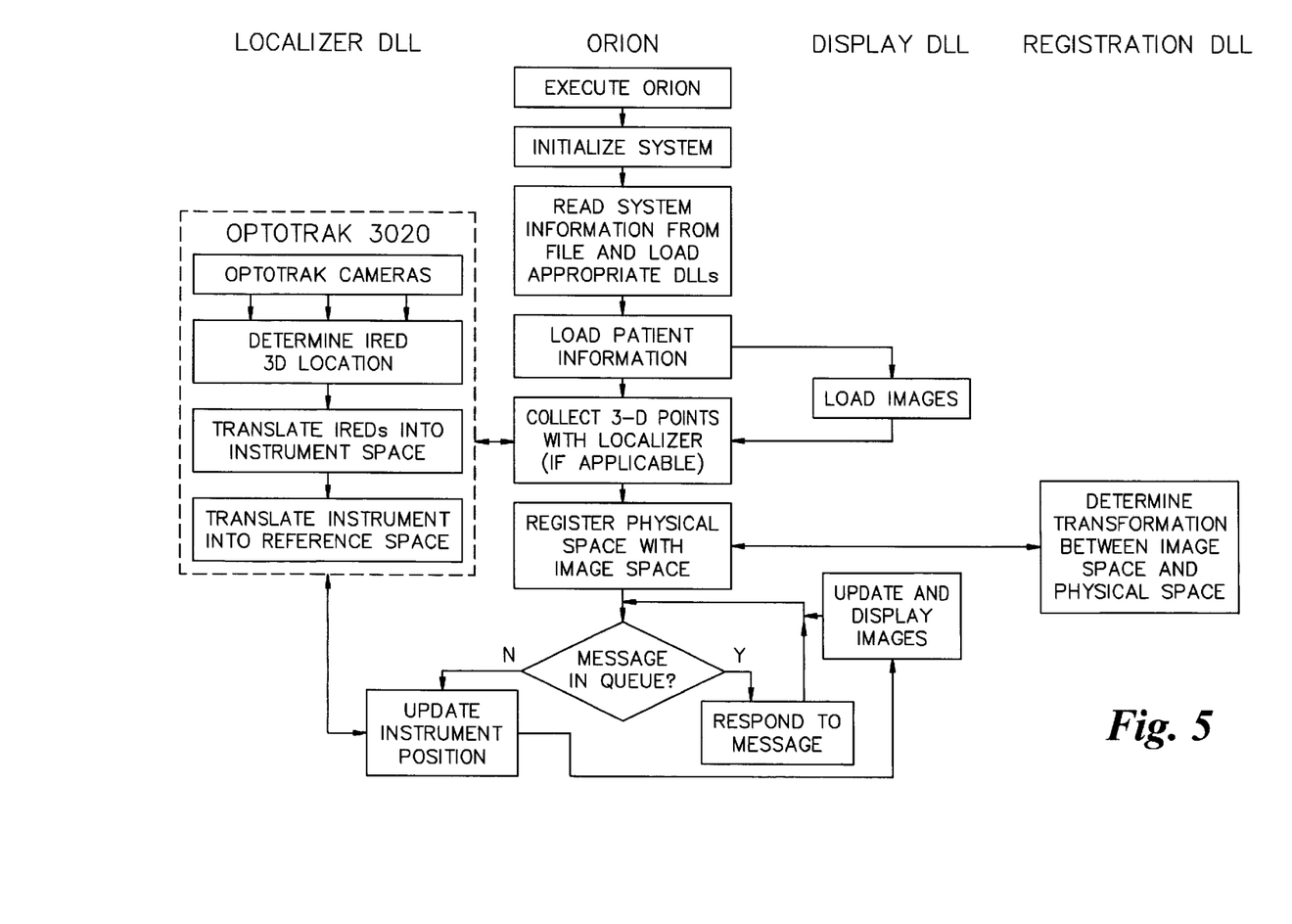
FIG. 5 a flow chart for software used by the present invention.

FIG. 5 shows a software cycle for image-guided surgery in accordance with the present invention. After execution in Windows NT, the system is initialized and all appropriate DLLs are loaded. A patient information file is then selected from a database. This file contains a list of files indicating image sets that are available for the particular surgical case. Each image set has an associated information file which is included in the patient file. This image information file contains a path to the actual image data, a tag to identify the appropriate DLL for its display, various parameters needed to visualize the data, and all registration types and corresponding image data needed for mapping physical space to image space. Once the image sets are loaded and their child window location is determined, it is usually appropriate to collect some type of physical space data using the localizer DLL. This data may be surface points or fiducial points which can be used in the surface-based or point-based registration algorithms described previously. Physical space and image space data is passed to the appropriate registration DLL and a mapping in the form of a matrix is returned to the present invention. Following registration between physical space and image space, the image sets or other display type is then visualized in some or all of the four child windows. The present invention then enters its message loop and maintains a message queue. The program is now ready to receive any keyboard or mouse input from the user. If there is a message in the queue, the present invention responds to the message and checks for other messages. There is "dead time" in the present invention when the program is idle waiting for messages (e.g., keyboard and mouse inputs). If no messages exist in the queue, the present invention receives matrix information from the localizer DLL concerning the current position of the probe(s) in physical space and passes this and any registration matrices to the appropriate display DLLs. The display DLLs map this physical space position into image space using the appropriate registration result and display the updated images, along with a colored circle to indicate current surgical position.

There are several pushbuttons and mouse commands in the present invention that produce messages. For example, if the user presses the right mouse key in a tomogram display window, the window and level of the image volume can be adjusted. The surgeon can also perform another type of registration, collect some type of physical space data with the tracked instrument, or change the display by pressing one of several pushbuttons on the main window. Each of these tasks are kept behind the simple pushbutton so that during surgery the physician can concentrate on the images displayed. As in the first example, the present invention receives a mouse click over a pushbutton as a message and responds to this request before updating the probe position and the images.

Interactive, image-guided surgery is being utilized in more and more applications, including neurosurgery, spinal surgery, and endonasal surgery. The present invention can be used for general surgical applications, including hepatic surgery.

Surgical treatment of hepatic tumors is performed by removal or ablation of involved segments of the liver. These tumors are localized by preoperative imaging studies, primarily CT imaging, intra-operative ultrasound and palpation. Of these localization techniques only the preoperative tomograms provide high-resolution, 3-D views of the tumor and the surrounding anatomy. However, at present, the tomographic information cannot be actively utilized for surgical guidance in the operating room. Thus, surgeons use other methods for operative tumor localization. It is especially important to accurately localize the tumor during liver ablation procedures, where precise probe placement within the volumetric center of a tumor is critical in the radiofrequency (heat-kill) or cryoablation (freeze-thaw) of the lesion. It is believed that the development of the present invention for hepatic surgery will improve both open and minimally invasive resection and ablation procedures in the liver. Minimally invasive hepatic surgery is currently conducted on a very limited basis. An endoscopic-IIGS system would combine the strengths of real time video imaging and the tomographic guidance from IIGS and make these procedures feasible. Deep-seated tumors which are indicated on CT images will be mapped onto video images of the liver surface using the direct linear transformation (DLT) and then displayed to allow the surgeon more accuracy in performing resections or ablative procedures under endoscopic guidance.

The present invention has been used in the laboratory on phantom livers. These model livers were constructed with rubber silicone, which was poured into a plaster mold along with spherical "tumors" constructed from cork. CT images of the phantom were acquired and a surface was created for registration purposes. The surface of the liver is digitized using the tracked probe and the present invention. The registration of the digitized liver surface to the surface of the liver created from the CT scan was calculated using an implementation of the iterative closest point registration algorithm. Experiments using the phantom liver and the described registration technique produced an average registration error of 1.8 mm. This surface registration calculation and the tracked RF probe have been used to localize the centers of "tumors" within the phantom on the CT images, and it was possible to place the tip of the instrument to within 1.2–6.0 mm of tumor centroids. Errors in this range can be achieved using the surface of the liver intraoperatively.

Experiments have been also conducted to develop a surgical protocol for using the present invention for open hepatic resection in patients with liver tumors, and tracked points on the liver to determine respiratory associated hepatic movement. An ablative instrument was placed on three anatomical points on the liver. Approximately 950 localization points (x,y,z) were continuously collected using the present invention. Each patient (n=2) had >2800 localization points collected during continuous respiratory cycles with standard continuous mandatory ventilator cycling. The change in position of the tracked points with respiration was calculated relative to the resting base position of the liver. Average motion with respiration for all anatomical points was 10.3±2.5 mm.

Interactive, image-guided surgery has improved the quality and feasibility of many surgical procedures, including neurosurgery and ENT surgery. It is crucial that these systems provide measures of system performance in a manner which parallels the surgical process. The systems must provide fast and accurate registration processes to map physical space into image space, and must also include instruments which precisely indicate current surgical position. In addition, images must be displayed and updated in real time to allow ease in tracking structures across slices or surface renderings.

A Windows-based image-guided surgical system has been developed on a low cost personal computer with an active optical tracking system. The present invention was developed in Visual C++ with the Win32 API for windows management. Since the present invention was developed using a module library for each of the different components, code migration and maintenance is simplified. At any given time, a subtask contained within a particular DLL used in the system can be "checked out" of a Visual C++ SourceSafe database that stores the most recently edited master copy.

The present invention is capable of applications beyond neurosurgery, including open and minimally invasive hepatic procedures. Target errors on the order of 2 mm for the phantom registration studies were higher than those seen in clinical neurosurgical cases. This number is acceptable since the liver is much more homogeneous than the brain and higher accuracy is not as critical an issue.

The present invention may be implemented with any combination of hardware and software. If implemented as a computer-implemented apparatus, the present invention is implemented using means for performing all of the steps and functions described above.

The present invention can be included in an article of manufacture (e.g., one or more computer program products) having, for instance, computer useable media. The media has embodied therein, for instance, computer readable program code means for providing and facilitating the mechanisms of the present invention. The article of manufacture can be included as part of a computer system or sold separately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. Apparatus for collecting and processing physical space data for use while performing image-guided surgery, the apparatus comprising:
   (a) a probe instrument for collecting physical space data by probing a plurality of physical surface points of surgically exposed tissue of a living patient, the physical space data providing three-dimensional (3-D) coordinates for each of the physical surface points;
   (b) an ablative instrument for resecting or ablating a particular portion of the exposed tissue; and
   (c) an image data processor comprising a computer-readable medium holding computer-executable instructions for:
      (i) based on the physical space data collected by the probe instrument, determining point-based registrations used to indicate surgical position in both image space and physical space;
      (ii) using the point-based registrations to map into image space, image data describing the physical space of an ablative instrument used to perform the image-guided surgery, an ablation zone of the ablative instrument, the tissue, and a particular portion of the tissue to be resected or ablated; and
      (iii) updating the image data on a periodic basis.

2. The apparatus of claim 1, wherein the ablative instrument emits a plurality of intermittent infrared signals used to triangulate the position of the ablative instrument in 3-D image space, the signals being emitted from a plurality of infrared emitting diodes (IREDs) distributed over the surface of a handle of the ablative instrument in a spiraling fashion.

3. The method of claim 2, wherein the IREDs flash in time sequence.

4. The method of claim 3, wherein each IRED has a 60 degree transmission angle.

5. The apparatus of claim 1, further comprising:
   (d) a scanning device for scanning tissue of the patient to acquire, store and process a 3-D reference of tissue prior to the tissue being surgically exposed, wherein the image data processor creates a triangularized mesh based on the scanned tissue, determines the volumetric center of a particular portion of the tissue to be resected or ablated during the surgery, and implements an algorithm using the triangularized mesh and the physical space data collected by the probe instrument to determine the point-based registrations.

6. The apparatus of claim 5, wherein the algorithm is a Besl and Mackay iterative closest point (ICP) registration algorithm.

7. The apparatus of claim 5, wherein the scanning device is one of the following scanners: a computerized tomography (CT) scanner, a magnetic resonance imaging (MRI) scanner and a positron emission tomography (PET) scanner.

8. The apparatus of claim 1, wherein the ablative instrument has a tip comprising an ablation device.

9. The apparatus of claim 8, wherein the ablation zone extends 1 centimeter from the tip of the ablative instrument.

10. The apparatus of claim 1, wherein the probe instrument is swept over the surface of the exposed tissue.

11. The apparatus of claim 1, wherein the image data is updated in real time at 30 Hz or greater.

12. The apparatus of claim 1, wherein the ablative instrument uses one of radio-frequency and cryoablation to resect or ablate the particular portion of the tissue.

13. The apparatus of claim 1, wherein points from 3-D physical space are mapped to 2-dimensional (2-D) image space.

14. The apparatus of claim 1, wherein points from 3-D physical space are mapped to 2-dimensional (2-D) laparoscopic video space using a direct linear transformation (DLT).

15. The apparatus of claim 1, wherein points from 3-D physical space are mapped to 3-D tomographic image space.

16. The apparatus of claim 1, wherein points from 3-D physical space are mapped to 2-dimensional (2-D) endoscopic image space.

17. An article of manufacture for collecting and processing physical space data for use while performing image-guided surgery, the article of manufacture comprising a computer-readable medium holding computer-executable instructions for performing a method comprising:

(a) determining point-based registrations used to indicate surgical position in both image space and physical space by processing physical space data collected by probing a plurality of physical surface points of surgically exposed tissue of a living patient, the physical space data providing three-dimensional (3-D) coordinates for each of the physical surface points;

(b) using the point-based registrations to map into image space, image data describing the physical space of an ablative instrument used to perform the image-guided surgery, an ablation zone of the ablative instrument, the tissue, and a particular portion of the tissue to be resected or ablated; and (c) updating the image data on a periodic basis.

18. The article of manufacture of claim 17, wherein the computer-executable instructions perform a method further comprising:

(d) creating a triangularized mesh based on a 3-D reference of tissue of the patient, the 3-D reference being acquired, stored and processed prior to the tissue being surgically exposed;

(e) determining the volumetric center of a particular portion of the tissue to be resected or ablated during the surgery; and (f) implementing an algorithm using the triangularized mesh and the physical space data to determine the point-based registrations.

19. The article of manufacture of claim 18, wherein the algorithm is a Besl and Mackay iterative closest point (ICP) registration algorithm.

20. The article of manufacture of claim 17, wherein points from 3-D physical space are mapped to 2-dimensional (2-D) image space.

21. The article of manufacture of claim 17, wherein points from 3-D physical space are mapped to 2-dimensional (2-D) laparoscopic video space using a direct linear transformation (DLT).

22. The article of manufacture of claim 17, wherein points from 3-D physical space are mapped to 3-D tomographic image space.

23. The article of manufacture of claim 17, wherein points from 3-D physical space are mapped to 2-dimensional (2-D) endoscopic image space.

24. A method of collecting and processing physical space data for use while performing image-guided surgery, the method comprising:

(a) surgically exposing tissue of a living patient;

(b) collecting physical space data by probing a plurality of physical surface points of the exposed tissue, the physical space data providing three-dimensional (3-D) coordinates for each of the physical surface points;

(c) based on the physical space data collected in step (b), determining point-based registrations used to indicate surgical position in both image space and physical space;

(d) using the registrations determined in step (c) to map into image space, image data describing the physical space of an ablative instrument used to perform the image-guided surgery, an ablation zone of the instrument, the tissue, and a particular portion of the tissue to be resected or ablated; and (e) updating the image data on a periodic basis.

25. The method of claim 24, wherein the ablative instrument emits a plurality of intermittent infrared signals used to triangulate the position of the ablative instrument in 3-D image space, the signals being emitted from a plurality of infrared emitting diodes (IREDs) distributed over the surface of a handle of the ablative instrument in a spiraling fashion.

26. The method of claim 25, wherein the IREDs flash in time sequence.

27. The method of claim 26, wherein each IRED has a 60 degree transmission angle.

28. The method of claim 24, further comprising:

(f) prior to surgery, scanning tissue of the patient to acquire, store and process a 3-D reference;

(g) creating a triangularized mesh based on the scanned tissue; and (h) determining the volumetric center of a particular portion of the tissue to be resected or ablated during the surgery, wherein an algorithm using the triangularized mesh and the physical space data collected in step (b) is implemented to determine the registrations in step (c).

29. The method of claim 28, wherein the algorithm is a Besl and Mackay iterative closest point (ICP) registration algorithm.

30. The method of claim 28, wherein step (f) is performed by one of a computerized tomography (CT) scanner, a magnetic resonance imaging (MRI) scanner and a positron emission tomography (PET) scanner.

31. The method of claim 24, wherein the ablative instrument has a tip comprising an ablation device.

32. The method of claim 31, wherein the ablation zone extends 1 centimeter from the tip of the ablative instrument.

33. The method of claim 24, wherein step (b) comprises sweeping an optically tracked localization probe over the surface of the exposed tissue.

34. The method of claim 24, wherein the tissue is the patient's liver and the particular portion of tissue to be resected or ablated is a hepatic metastatic tumor.

35. The method of claim 24, wherein the image data is updated in real time at 30 Hz or greater.

36. The method of claim 24, wherein the ablative instrument uses one of radio-frequency and cryoablation to resect or ablate the particular portion of the tissue.

37. The method of claim 24, wherein points from 3-D physical space are mapped to 2-dimensional (2-D) image space.

38. The method of claim 24, wherein points from 3-D physical space are mapped to 2-dimensional (2-D) laparoscopic video space using a direct linear transformation (DLT).

39. The method of claim 24, wherein points from 3-D physical space are mapped to 3-D tomographic image space.

40. The method of claim 24, wherein points from 3-D physical space are mapped to 2-dimensional (2-D) endoscopic image space.

* * * * *